United States Patent
Hirota et al.

(10) Patent No.: US 8,293,944 B2
(45) Date of Patent: *Oct. 23, 2012

(54) REACTION APPARATUS

(75) Inventors: Atsushi Hirota, Wakayama (JP); Toru Nishimura, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/353,359

(22) Filed: Jan. 19, 2012

(65) Prior Publication Data

US 2012/0123167 A1    May 17, 2012

Related U.S. Application Data

(60) Continuation of application No. 12/852,564, filed on Aug. 9, 2010, now Pat. No. 8,119,843, which is a division of application No. 11/144,708, filed on Jun. 6, 2005, now abandoned.

(30) Foreign Application Priority Data

Jun. 11, 2004 (JP) ................................. 2004-173620

(51) Int. Cl.
  *B01J 19/18* (2006.01)
  *B01J 19/00* (2006.01)
  *C07C 209/00* (2006.01)

(52) U.S. Cl. ........ 564/479; 422/222; 422/224; 422/225; 422/228; 564/478

(58) Field of Classification Search .................. 422/222, 422/224, 225, 228; 564/479, 478
See application file for complete search history.

(56) References Cited

U.S. PATENT DOCUMENTS

| 4,138,437 | A | 2/1979 | Strauss et al. |
| 5,791,780 | A | 8/1998 | Bakker |
| 6,086,832 | A | 7/2000 | Ohta |
| 7,351,866 | B2 | 4/2008 | Hirota et al. |
| 7,615,666 | B2 | 11/2009 | Nishimura et al. |
| 8,119,843 | B2 * | 2/2012 | Hirota et al. .................. 564/479 |
| 2002/0081254 | A1 | 6/2002 | Boger |
| 2003/0157003 | A1 | 8/2003 | Machado et al. |
| 2008/0004472 | A1 | 1/2008 | Nishimura et al. |
| 2010/0217044 | A1 | 8/2010 | Nomura et al. |

FOREIGN PATENT DOCUMENTS

CN    86 2 02953 U    7/1987

(Continued)

OTHER PUBLICATIONS

Office Action issued Apr. 20, 2011, in Chinese Patent Application No. 200510076740.4, filed Jun. 10, 2005 (with English translation).

(Continued)

*Primary Examiner* — Walter D Griffin
*Assistant Examiner* — Lessanework Seifu
(74) *Attorney, Agent, or Firm* — Oblon, Spivak, McClelland, Maier & Neustadt, L.L.P.

(57) ABSTRACT

A reaction apparatus which is used for conducting a gas-liquid chemical reaction in a state that a liquid is in a continuous phase, wherein its reactor has therein a shear type stirring impeller for dispersing a raw reaction gas or a carrier gas and a film-formed catalyst, which apparatus is capable of producing a target reaction product; and a process for producing a tertiary amine in such reaction apparatus.

3 Claims, 4 Drawing Sheets

| | FOREIGN PATENT DOCUMENTS | | |
|----|----|----|----|
| CN | 1288777 | A | 3/2001 |
| CN | 2695842 | Y | 4/2005 |
| CN | 1863597 | A | 11/2006 |
| JP | 6211754 | | 8/1994 |
| JP | 2003-176255 | A | 6/2003 |
| JP | 2003-275577 | A | 9/2003 |
| WO | 2005/035122 | | 4/2005 |

OTHER PUBLICATIONS

Chemical Engineering Manual, vol. 5, Chum and Mizture, Published by Chemical Industrial Press, 2 pages (10985).

* cited by examiner

REACTION APPARATUS

This is a continuation application of U.S. application Ser. No. 12/852,564, filed Aug. 9, 2010, which is a divisional application of U.S. application Ser. No. 11/144,708, filed Jun. 6, 2005.

FIELD OF THE INVENTION

The present invention relates to a reaction apparatus wherein a film-formed catalyst is used to conduct a gas-liquid chemical reaction in the state that a liquid is in a continuous phase, in particular, a reaction apparatus which is suitably used when an alcohol and a primary or secondary amine are used as starting materials to produce the corresponding tertiary amine.

BACKGROUND OF THE INVENTION

A great number of industrial reactions are conducted in mixing-chamber type reaction apparatus wherein a solid catalyst is made into a slurry and used. The catalyst made into the slurry is made of fine powder. In the presence of the catalyst, a reactive gas such as hydrogen or ammonia is brought into contact with a liquid to conduct reaction. When the reaction ends, the catalyst is generally removed by filtration, so as to collect the reaction product.

However, a catalyst in a slurry form has problems about safety, an increase in wastes, operability, productivity and so on. For example, one of the problems is a problem that many catalysts are naturally ignitable, thereby causing an anxiety about safety. A second one thereof is a problem that the catalyst generally needs to be removed by filtration in order to collect a reaction product, thereby making facilities therefor and the operation thereof complicated.

An example of a production process which neither needs any mixing operation, such as stirring or gas bubbling, nor any separation of a catalyst by filtration is a fixed bed process. As the catalyst used in the fixed bed process, there have been hitherto well-known molded catalysts such as pellet-form, noodle-form or tablet-form catalysts. The catalysts are each a catalyst wherein a powdery material having catalyst activity is molded into any one of the above-mentioned forms by compression, extrusion or some other method, thereby forming a structure having therein countless pores so as to make the form of bulk compatible with a high surface area. The process is disclosed in, for example, JP-A-6-211754.

As a different method for fixing a catalyst, known is a method of forming a thin catalyst layer in a film form inside a reaction field. For example, JP-A-2003-176255 discloses a reactor wherein a catalyst metal is caused to adhere onto the surface of a monolith. Therein, the following advantage is indicated: in a hydrogenating reaction between a reactant gas and a reactant liquid, a drop in the pressure inside the reactor is small so that speeds of the gas and the liquid can be made large; therefore, the mass transfer therein is further promoted than in fixed bed filled reactors of conventional types.

A different reactor using a monolith catalyst is disclosed in JP-A-2003-275577. In order to improve the solubility of a reactant gas into a reactant liquid, the gas is finely dispersed by the rotation of a turbine impeller fitted onto a housing into which the catalyst is put, and in order to control the convection state of the reactant liquid, a baffle is used. In this way, the selectivity of a hydrogenation reaction for producing aniline from nitrobenzene is improved.

SUMMARY OF THE INVENTION

The present invention provides a reaction apparatus for conducting a gas-liquid chemical reaction in the state that the liquid forms a continuous phase, provided with a film-formed catalyst and a shear type stirring impeller for dispersing a raw reaction gas or a carrier gas.

The present invention provides a process for producing a tertiary amine, comprising the step of reacting a primary or secondary amine with an alcohol in the above defined reaction apparatus.

The present invention further provides use of the above shown reaction apparatus for conducting a gas-liquid chemical reaction in the state that the liquid forms a continuous phase and a raw reaction gas or a carrier gas is dispersed.

BRIEF DESCRIPTION OF THE DRAWINGS

FIG. 5(a) and FIG. 5(b) are a front view thereof and a plan view thereof, respectively;

Figure 1:
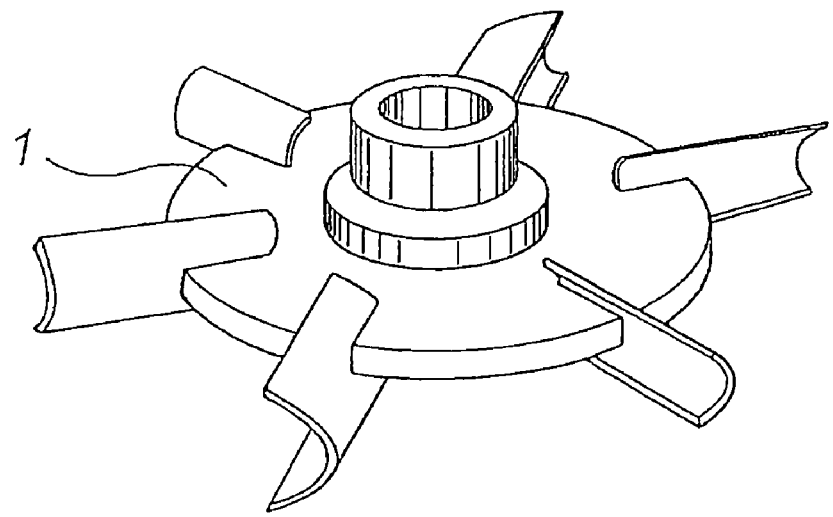
FIG. 1 is a perspective view illustrating an example of a concave turbine which is a shear type stirring impeller used in the present invention.

REFERENCE NUMERALS IN THE DRAWINGS ARE EXPLAINED 1 concave turbine
11 edged turbine
2 reactor (separable flask)
3 film-formed catalyst
4 casing
5 baffle
6 glass tube
7 propeller blade

DETAILED DESCRIPTION OF THE INVENTION

A reaction manner as described in JP-A-6-211754 solves many problems about the handling of a catalyst or wastes, but cannot be applied to many reactions on the basis of technical problems. One of the problems is that in reactions followed by the generation of heat, a problem is caused in the control of a rise in the temperature of the whole and the gradient of the temperature. Another problem is caused in the distribution of the liquid and gas in a reactor. An insufficient conversion ratio and a localized concentration gradient are often generated so as to promote a side reaction.

In JP-A-2003-176255, a static mixer is used in order to distribute gas. It is difficult to apply or divert a mixing-chamber type reactor used in a slurry catalyst system reaction, as it is, to this technique.

In JP-A-2003-275577, the convection of a liquid is positively performed. Therefore, this technique has a problem that the time when gas is retained in a catalyst layer is decreased so that the time when the gas is dissolved into the liquid becomes short.

The present invention provides a reaction apparatus which is used for gas-liquid chemical reaction and is capable of producing a target reaction product with a high yield by a simple process.

According to the reaction apparatus of the present invention, a target material can be obtained with a high yield by a simple process wherein no catalyst-separating-operation is necessary.

The gas-liquid chemical reaction of the present invention means a chemical reaction, such as addition reaction, hydrogenation reaction or dehydrogenation reaction, which is conducted by blowing a raw reaction gas or a carrier gas into a place where a liquid is in a continuous phase.

The film catalyst used in the present invention means a catalyst in the form of a thin film having a thickness of 1 mm or less, which is different from any conventional irregularly-filled type having a size of about several millimeters. The process in raw reaction materials and a reaction product are transferred inside the catalyst is controlled by diffusion. When the distance therefor is made short to 1 mm or less, mass transfer between the inside and the outside of the catalyst can be promoted so as to suppress any excessive reaction of reaction intermediate materials inside the catalyst. In particular, the thickness is preferably 100 µm or less, more preferably 50 µm or less. The lower limit of the thickness is preferably 0.01 µm or more, more preferably 1 µm or more in order to keep the strength of the catalyst layer surely and give endurance in strength thereto.

About the structure of the film-formed catalyst, it is necessary that the structure is a structure wherein the supply of raw reaction materials to the body of the catalyst and the collection of a product from the catalyst body can easily be performed. In order to advance the reaction effectively, it is desired to make the surface of the catalyst body, where the supply of the raw reaction materials and the collection of the product are performed, as wide as possible. In order to attain this requirement, the following is preferably used: an object wherein the film-formed catalyst is fitted onto the inner wall face of a set wherein tubes having an inside diameter of several millimeters to several tens of millimeters are bundled or a honeycomb structure having a cell density of several tens to several hundreds of cells per square inch; or the like.

In order to make the film-formed catalyst into the above-mentioned various structures, for example, a method of molding a catalyst active material itself into a honeycomb-form structure and other methods can be considered. From the viewpoint of making a thin catalyst layer compatible with a high mechanical strength, it is preferred to fix the film-formed catalyst onto the surface of a support. Examples of the method therefor include a method of forming a coating layer containing a catalyst active material onto the surface of a metal or a support having rigidity, in the form of a tube, flat plate, honeycomb or the like, thereby preparing the film-formed catalyst. As the coating method at this time, a method known in the prior art can be used. Examples thereof include physical vapor deposition methods such as sputtering, chemical vapor deposition methods, a method of impregnation from a solution system, and various coating methods such as blade, spray, dip, spin, gravure, and die coating methods, using a binder.

The internal structure of the film-formed catalyst depends largely on the kind of the active material constituting the catalyst body, the method for producing the catalyst body, and so on, and may be made of a dense continuous phase or may be porous. For example, in the case of a thin film formed on the surface of a support by sputtering, chemical vapor deposition or the like, the thin film can be made into a dense continuous phase. In the case of using a powdery active material to form a film onto the surface of a support by wet or dry coating or some other method, the film can be made porous.

The film-formed catalyst may contain therein a binder for fixing the active material therein to form the film-formed catalyst body. The binder itself does not act as an active material. The binder may be any polymer or inorganic material that has not only a property for binding the active material particles or binding the binder to the support surface but also chemical resistance, heat resistance and other natures for resisting reaction environment and producing no bad effect to the reaction system. Examples thereof include cellulose resins such as carboxymethylcellulose and hydroxyethylcellulose, fluorine-contained resins such as poly(tetrafluoroethylene) and poly(vinylidenefluoride), urethane resins, epoxy resins, polyester resins, phenol resins, melamine resins, silicone resins, and other polymer compounds; and sols of inorganic compounds such as silica and alumina.

As the type of the reactor into which the film-formed catalyst is fitted, various types, including types known in the prior art, can be adopted if the types make it possible to carry out stirring with a stirring impeller.

The distribution and supply of a gas into the film-formed catalyst layer are performed while fine air bubbles are formed with the stirring impeller. At this time, in order to make the retention time of the gas long, it is desired not to force out the liquid in the axial direction or the circumferential direction by the stirring, so as to suppress the convection of the liquid with the stirring impeller. For this purpose, in the present invention, a shear type stirring impeller is used which make the following possible: fine air bubbles are formed by shear force; the interfacial area between the gas and the liquid is increased to promote diffusion; and the retention time of the air bubbles is made long since rising speed of the air bubbles becomes small.

Figure 2:
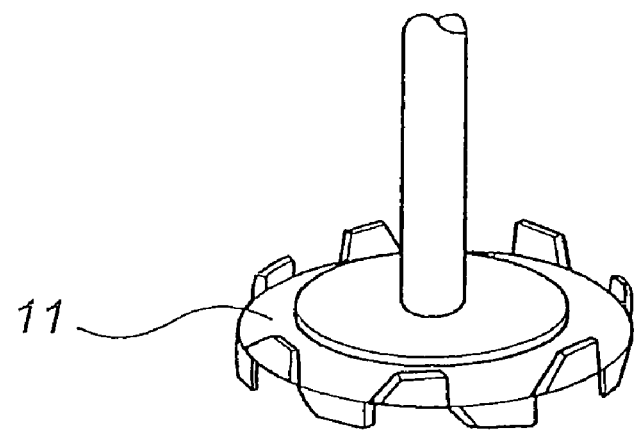
FIG. 2 is a perspective view illustrating an edged turbine which is a shear type stirring impeller used in the present invention.
Figure 5:
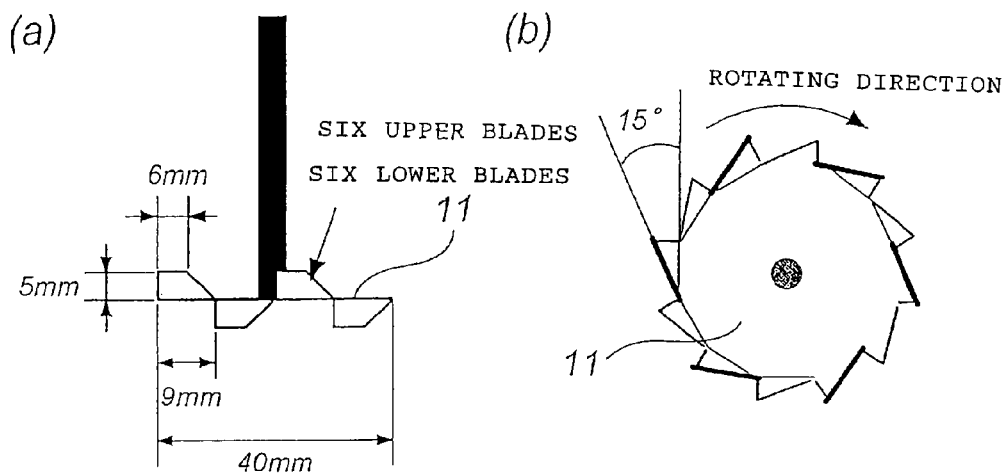
FIG. 5 are views illustrating an edged turbine used in Example 1.

The shear type stirring impeller herein means a stirring impeller having a relatively high shear power for the jetting-out power thereof. Examples thereof include a flat turbine, a concave turbine, and an edged turbine. The concave turbine and the edged turbine are preferred. The concave turbine is a stirring impeller 1 defined in U.S. Pat. No. 5,791,780 and others, as illustrated in FIG. 1. The edged turbine is a stirring impeller 11 having such a form that blades are fitted substantially perpendicularly to a disc and further the angle of the blades to the circumferential direction is from 0 to 30°, and is specifically illustrated in FIGS. 2 and 5. It is desired that the positions of the blades are below the lower end of the catalyst layer in order to supply the gas effectively to the catalyst layer.

As the method for supplying a gas to be dispersed by stirring to the film-formed catalyst layer, there can be adopted various methods, examples of which include methods known in the prior art, such as a single tube type sparger and a ring type sparger. A supply opening for the gas may be positioned in any one of the upside, the downside and the side of the impeller. In order to make the gas minute effectively and disperse the gas, it is preferred that the gas is blown out toward the downside of the impeller.

Figure 3:
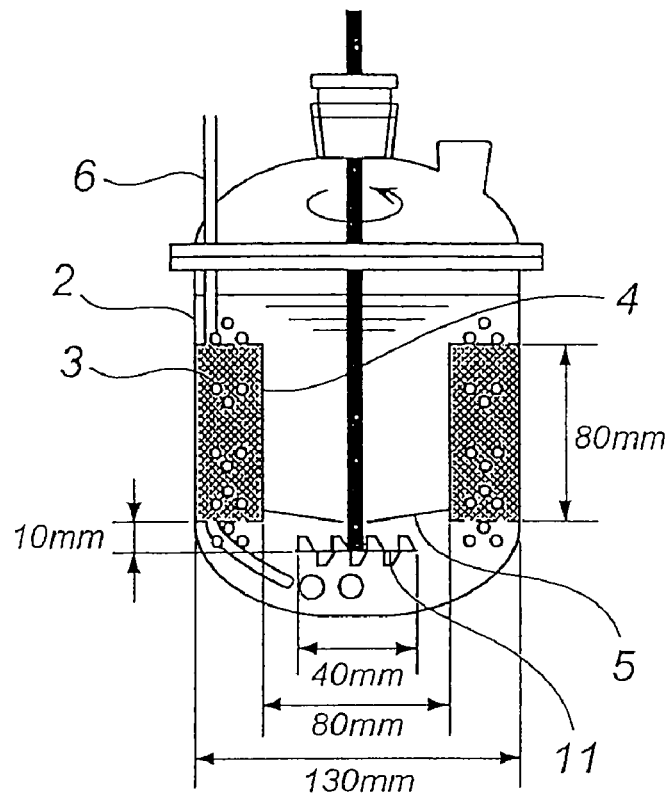
FIG. 3 is a front view of a reaction apparatus used in Example 1.

As illustrated in FIG. 3, the method for fitting the film-formed catalyst into the reactor is preferably such an arrangement in a doughnut form that the film-formed catalyst 3 is fitted to the vicinity of a wall surface of the reactor 2. In the arrangement, it is preferred to use a casing 4 for fixing the catalyst. An inner cylinder of the casing is preferably provided with a baffle 5 so that the gas is induced not to flow through the central region of the reactor where the catalyst is not placed and the liquid is suppressed from convection.

Figure 4:
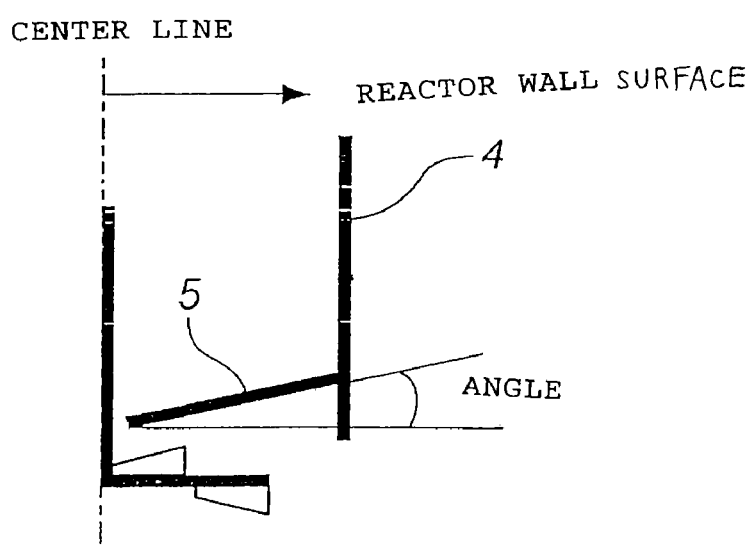
FIG. 4 is an enlarged view of a baffle section of the reaction apparatus illustrated in FIG. 3.

Furthermore, it is preferred to cause this baffle 5 to have an escalation angle from the central region toward the wall face of the reactor, as illustrated in FIG. 4, in order not to cause any retention of the gas.

The reaction apparatus of the present invention can be used suitably for reaction for producing a tertiary amine from a primary or secondary amine and an alcohol.

The alcohol as the starting material used to produce a tertiary amine is preferably a linear or branched, saturated or unsaturated aliphatic alcohol having 6 to 36 carbon atoms. Examples thereof include hexyl alcohol, octyl alcohol, lauryl alcohol, myristyl alcohol, stearyl alcohol, behenyl alcohol and oleyl alcohol; mixed alcohols thereof; Ziegler alcohols obtained by the Ziegler process; and oxo alcohols and Guerbet alcohols obtained by the oxo process.

The primary or secondary amine used when a tertiary amine is produced is preferably an aliphatic primary or secondary amine. Examples thereof include methylamine, dimethylamine, ethylamine, diethylamine, dodecylamine, and didodecylamine.

The corresponding tertiary amine obtained from the alcohol and the primary or secondary amine, which are starting materials, is a substance wherein the hydrogen atom (s) bonded to the nitrogen atom in the primary or secondary amine is/are substituted with one or more alkyl and/or alkenyl group(s) derived from the alcohol. For example, the corresponding tertiary amine obtained from lauryl alcohol and dimethylamine is N-dodecyl-N,N-dimethylamine, and is distinguished from N,N-didodecyl-N-methylamine and N,N,N-tridodecylamine, which are each a tertiary amine as a byproduct resulting from reaction with methylamine and ammonia, both of which are produced by disproportionation of dimethylamine.

The active material which constitutes the film-formed catalyst is not limited to especial kind, and may be any known active material. In the case that an alcohol and a primary or secondary amine are used as starting materials to produce the corresponding tertiary amine, a Cu-based material or the like can be preferably used. Examples thereof are Cu alone, or metals made of two or more components wherein one or more transition metal elements, such as Cr, Co, Ni, Fe and/or Mn, is/are to Cu. Examples thereof are also substances wherein these are further carried on silica, alumina, titania, zeolite or the like.

When a tertiary amine is produced, it is desired that the pressure in the system is not remarkably high over normal pressure. The reaction temperature is varied dependently on the kind of the catalyst, and the reaction is conducted preferably at a temperature of 150 to 300° C. In the case that byproduct water produced in the process of the reaction is discharged out of the reaction system, the advance of the reaction can be promoted and the activity of the catalyst can be kept.

The use of the reaction apparatus of the present invention makes it possible to yield a target reaction product with a high yield, in a gas-liquid chemical reaction in the state that a liquid is in a continuous phase, by a simple process.

EXAMPLES

Then examples according to the present invention will be explained. These examples are intended to describe preferred embodiments of the present invention and are not intended to be limiting of the invention.

Production Example 1

Production of a Film-Formed Catalyst

A film-formed catalyst made of a three-component copper-nickel-ruthenium catalyst active material and carried on synthetic zeolite was prepared as follows.

Synthetic zeolite was charged into a flask having a volume of 1 L, and subsequently thereinto was put a solution wherein copper nitrate, nickel nitrate and ruthenium chloride were dissolved in water in such a manner that the ratio by mole between the metal atoms therein would satisfy: Cu:Ni:Ru=4:1:0.01. While the solution was stirred, the temperature thereof was raised. An aqueous 10% by weight $Na_2CO_3$ solution was dropwise added slowly at 90° C. to the solution while the pH thereof was controlled into the range of 9 to 10. The solution was ripened for 1 hour, and subsequently the resultant precipitation was filtrated, washed with water, dried at 80° C. for 10 hours, and then calcined at 600° C. for 3 hours to yield a powdery catalyst active material. The ratio of metal oxides in the resultant catalyst active material was 33% by weight, and the ratio of synthetic zeolite was 67% by weight.

To 31 parts by weight of the catalyst active material were added 38 parts by weight of a phenol resin (PR-50626 manufactured by Sumitomo Bakelite Co., Ltd.; solid content: 44 parts by weight), and then the mixture was put together with 31 parts by weight of acetone into a 50-mL wide-mouthed polyethylene bottle (AS ONE Corporation). The resultant was made into a paint with a paint shaker. This paint was applied onto a copper foil (thickness: 35 μm, 12 cm×300 cm) as a support with a bar coater, and then at 150° C. drying and the hardening of the resin were performed for 15 minutes to fix the film-formed catalyst 10 μm in thickness onto both surfaces of the copper foil. The weight of the film-formed catalyst excluding the copper foil was 5.6 g (including the weight of the binder).

Example 1

The reaction apparatus illustrated in FIG. 3 was used to conduct the following reaction.

A part of the film-formed catalyst obtained in Production Example 1 were folded into waved plates, and the wave plates and the remaining flat plates were alternately wounded in layers and arranged into the form of a doughnut having an inside diameter of 80 mm and an outside diameter equal to the inside diameter (inside diameter: 130 mm) of the 2-L separable flask 2 made of glass. The volume of the region 3 into which the film-formed catalyst was fitted was 660 mL. The film-formed catalyst was thus formed to have plural channels being continuous through the axial direction of the separable flask 2. Each channel had a cross-section area of about 0.1 $cm^2$. Into the separable flask 2 was charged 1200 g of dodecyl alcohol (Kalcol-2098, manufactured by Kao Corp.), and then hydrogen gas was blown in at a rate of 20 L/h, the rate being calculated in terms of the standard state volume thereof, from the bottom of the separable flask 2 through a glass tube 6 having an outside diameter of 6 mm and a thickness of 1 mm. The edged turbine 11 having an impeller diameter of 40 mm, illustrated in FIG. 5, was used to stir the solution at a rotation number of 800 rpm while raising the temperature of the solution. The position where the edge turbine was set up was a position 1 cm apart from the downside of the catalyst layer 3.

The catalyst was subjected to reduction activation. Thereafter, while the flow rate of the hydrogen gas was maintained, dimethylamine gas started to be blown in through the glass tube 6. Furthermore, the temperature was raised up to 220° C. The time when the temperature reached 220° C. was decided as reaction zero time, and reaction was started. The reaction pressure was set to normal pressure, and water produced by the reaction was continuously removed out of the system through a rectifying tower. During the reaction, the stirring speed, the temperature inside the system and the flow rate of the hydrogen gas were maintained. The flow rate of the dimethylamine gas was made a constant value of 200 g/h before the amount of unreacted dodecyl alcohol turned into 10% as an area-percentage value analyzed by gas chromatography. When the value was 10% or less, the flow rate was lowered to 80 g/h as the constant flow rate. Furthermore, at the time when the amount of unreacted dodecyl alcohol was 10% or less, $N_2$ gas was supplied at a constant rate of 48 L/h. During the reaction, the reaction was traced by the above-mentioned gas chromatography. The yield of the product excluding any byproduct when the amount of unreacted alcohol was 1% was obtained from gas chromatographic data before and after this time. The results are shown in Table 1.

Comparative Example 1

Figure 8:
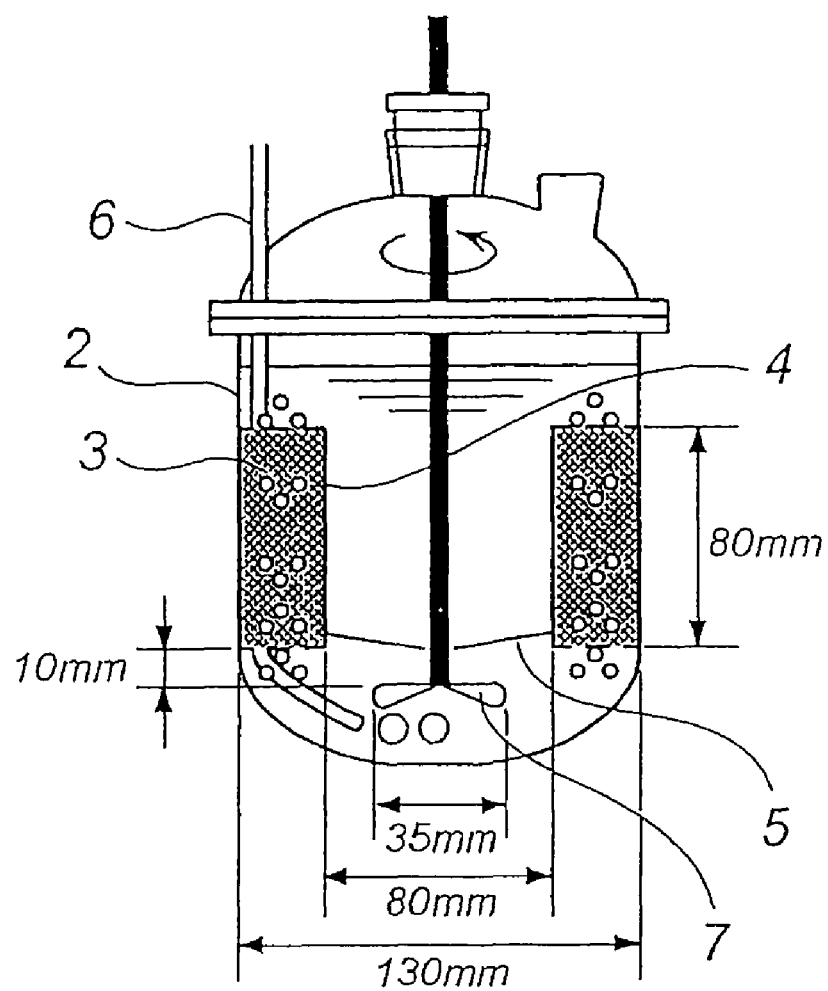
FIG. 8 is a front view of a reaction apparatus used in Comparative Example 1.

A reaction apparatus illustrated in FIG. 8 was used to conduct the following reaction.

Figure 6:
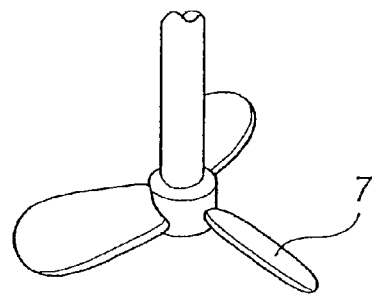
FIG. 6 is a perspective view illustrating a propeller impeller used in Comparative Example 1.
Figure 7:
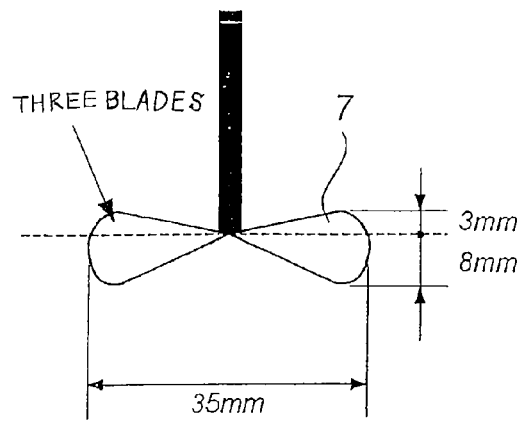
FIG. 7 is a front view of the propeller impeller used in Comparative Example 1.

Specifically, propeller blades 7 illustrated in FIGS. 6 and 7 were used instead of the edged turbine 1 in the reaction apparatus used in Example 1 to disperse gas. Reaction was conducted through the same steps as in Example 1 except that the rotation number was set to 620 rpm so as to make the stirring power equal to that of the edged turbine when hydrogen gas was caused to pass at 20 L/h. In this case, the yield of the product excluding any byproduct when the amount of unreacted alcohol was 1% is shown in Table 1. The byproduct was generated in a larger amount than in Example 1. Consequently, the yield was low.

TABLE 1

|  | Example 1 | Comparative example 1 |
|---|---|---|
| Alcohols as starting material | Dodecyl alcohol 1200 g | Dodecyl alcohol 1200 g |
| Reaction temperature | 220° C. | 220° C. |
| Kind of catalyst | Film-formed catalyst of Production example 1 | Film-formed catalyst of Production example 1 |
| Weight of film-formed catalyst (including binder) | 5.6 g | 5.6 g |
| Catalyst arranging method | Doughnut form φ130 mm/φ80 mm | Doughnut form φ130 mm/φ80 mm |
| Gas dispersing method | Glass tube φ6 mm + Edged turbine | Glass tube φ6 mm + Propeller blades |
| Rotation number | 800 rpm | 620 rpm |
| Power | 0.0698 kg · m$^2$/s$^3$ | 0.0698 kg · m$^2$/s$^3$ |
| H$_2$ flow rate | 20 L/h | 20 L/h |
| Flow rate of dimethylamine | 200 g/h constant when an unreacted alcohol amount is more than 10% →80 g/h constant in the unreacted alcohol amount of 10% or less | 200 g/h constant when an unreacted alcohol amount is more than 10% →80 g/h constant in the unreacted alcohol amount of 10% or less |
| N$_2$ flow rate | 48 L/h constant in the unreacted alcohol amount of 10% or less | 48 L/h in the unreacted alcohol amount of 10% or less |
| Yield*[1] | 90.0% | 87.6% |

*[1] content of pure N-dodecyl-N,N-dimethylamine

The invention claimed is:

1. A process for producing a tertiary amine, comprising reacting a primary or secondary amine with an alcohol, in a reaction apparatus provided with a shear producing stirring impeller, by conducting a gas-liquid chemical reaction with a film-formed catalyst in a state that the liquid forms a continuous phase, dispersing a raw reaction gas or a carrier gas with the impeller, wherein
   the alcohol is a linear or branched, saturated or unsaturated aliphatic alcohol having 6 to 36 carbon atoms,
   the primary or secondary amine is a primary or secondary aliphatic amine,
   the film-formed catalyst, which contains therein a binder for fixing active material therein to form the film-formed catalyst body, has a thickness of 1 mm or less.

2. The process for producing a tertiary amine according to claim 1, wherein the reaction apparatus has therein an inducement baffle for the raw reaction gas.

3. The process for producing a tertiary amine according to claim 1, wherein the thickness is 50 μm or less and 1 μm or more.

* * * * *